US008685406B2

(12) United States Patent
Walker et al.

(10) Patent No.: US 8,685,406 B2
(45) Date of Patent: Apr. 1, 2014

(54) COMPOSITIONS OF AND METHOD OF USING HEAT SHOCK PROTEIN PEPTIDES

(75) Inventors: David H. Walker, Galveston, TX (US); Sunil Thomas, Dickinson, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 421 days.

(21) Appl. No.: 12/927,220

(22) Filed: Nov. 10, 2010

(65) Prior Publication Data

US 2011/0117130 A1    May 19, 2011

Related U.S. Application Data

(60) Provisional application No. 61/281,178, filed on Nov. 13, 2009.

(51) Int. Cl.
*A61K 39/02* (2006.01)
*C07K 16/00* (2006.01)

(52) U.S. Cl.
USPC ................. 424/190.1; 424/192.1; 424/194.1; 424/195.11; 530/326

(58) Field of Classification Search
None
See application file for complete search history.

(56) References Cited

U.S. PATENT DOCUMENTS 7,309,583 B2 * 12/2007 Walker et al. ................ 435/69.1

FOREIGN PATENT DOCUMENTS

WO    98/23735    *   6/1998
WO    99/35270    *   7/1999

OTHER PUBLICATIONS

Sumner et al UniProt Database Accession No. O34194 (CH60_EHRCA), publically available 1998.*
Sumner et al UniProt Database Accession No. Q9KJ73 (Q9KJ73_9RICK) publically available 2000.*
Retzlaff, C. et al. Bacterial Heat shock Proteins Directly Induce Cytokine mRNA and Interleukin-1 Secreton in Macrophage Cultures: *Infection and Immunity*, 1994, vol. 62, No. 12, pp. 5689-5693.
Khan, N. M. et al. Immunogenicity and Protective Efficacy of GroEL (hsp60) of *Streptococcus pneumoniae* against Lethal Infection in Mice: *FEMS Immunol. Med. Microbiology*, 2009, vol. 56, pp. 56-62.
Bai, Y. et al. Expression of *Helicobacter pylori* Hsp60 Protein and its Immunogenicity: *World Journal of Gastroenterol*, 2003, vol. 9, No. 12, pp. 2711-2714.
Yamaguchi, H. et al. Effect of Bacterial Flora on Postimmunization Gastritis Following Oral Vaccination of Mice with *Helicobacter pylori* Heat Shock Protein 60: *Clinical and Diagnostic Laboratory Immunology*, Sep. 2003, vol. 10, No. 5, pp. 808-812.
Soares, R. B. A. et al. Vaccination With Heat Shock Protein 60 Induces a Protective Immune Response Against Experimental Paracoccidioides Brasiliensis Pulmonary Infection: *Infection and Immunity*, Sep. 2008, vol. 76, No. 9, pp. 4214-4221.
Paliwal, P. K. et al. Cloning, Expression and Characterization of Heat Shock Protein 60 (groEL) of *Salmonella enterica* Serovar Typhi and its role in Protective Immunity Against Lethal *Salmonella* Infection in Mice: *Clinical Immunology*, 2008, vol. 126, pp. 89-96.
Ahsan et al., FEBS Lett., 1991, 288:77-80.
Breitschwerdt, Obligate intracellular pathogens. In Ettinger, SJ; Feldman, EC (eds). Textbook of Veterinary Internal Medicine. W.B. Saunders Co. Philadelphia, PA; 2005; 30 631-632.
Buhles et al., J Infect Dis. 1974; 130:357-367.
Callebaut et al., C R Acad Sci III. 1994; 317:721-729.
Couto, Rickettsial Diseases. In Birchard et al., (eds.) Saunders Manual of Small Animal Practice. W.B. Saunders Co. Philadelphia, PA, 1994, 124-125.
Dawson et al., Am J Vet Res., 1996, 57:1175-1179.
Dawson et al., J Clin Microbial., 1994, 32: 2725-2728.
Galdiero et al., Infect Immun., 1997, 65: 699-707.
Harboe et al., Clin Exp Immunol., 1991, 86:2-5.
Harrus et al., Canine monocytic ehrlichiosis: An update. Compendium of Continuing Education for the Veterinary Practitioner, 1997, 19: 431-444.
Hayer-Hartl et al., EMBO J., 1996, 15:6111-6121.
Jaattela et al., Ann Med., 1992, 24:249-258.
Kyte et al., J Mol Biol., 1982, 157: 105-132.
Neer et al., J Vet Intern Med., 2002, 16: 309-315.
Netzer et al., Trends Biochem Sci., 1998, 23: 68-73.
Noll et al., Infect Immunity, 1996, 64:2955-2961.
Olson, Ehrlichiosis. In: Zoonoses updates from the Journal of the American Veterinary Medical Association. American Veterinary Medical Association. Schaumburg, IL, 1995:74-75.
Quintana et al., 12th International Congress of Immunology and 4th Annual Conference of FOCIS, 2004, 207-213.
Quintana et al., Arthritis Rheum., 2004, 50: 3712-3720.
Rikihisa et al., Microbes Infect., 1999, 1: 367-376.
Segal et al., Drug Discov Today, 2006, 11: 534-540.
Thomas et al., Parasite Immunol, 2009, 31: 296-303.
Tsan et al., J Leuk Biol., 2009, 85: 905-910.
Ueki et al., Clin Exp Immunol., 2002, 127: 72-77.
Wallin et al., Trends Immunol., 2002, 23: 130-135.
Woo et al., Clin Diagn Lab Immunol., 2001, 8: 832-836.
Young, Heat-shock proteins: immunity and autoimmunity, Curr Opin Immunol., 1992, 4: 396-400.

* cited by examiner

*Primary Examiner* — Patricia A Duffy

(57) ABSTRACT

The present invention provides an isolated and purified heat shock protein 60 (Hsp60) peptide having the amino acid sequence of SEQ ID NO:2. The instant invention is also directed to a vaccine against *Ehrlichia* comprising a peptide homologous to the amino acid sequence of SEQ ID NO:2. The instant invention is also directed to an antibody directed against a peptide homologous to the amino acid sequence of SEQ ID NO:2. The instant invention is also directed to a method of determining whether a subject is infected with *Ehrlichia*, comprising the steps of: contacting a sample from a subject with the antibody described herein; and detecting a resulting antibody reaction, wherein a positive reaction indicates the subject is infected with *Ehrlichia*.

12 Claims, 8 Drawing Sheets

COMPOSITIONS OF AND METHOD OF USING HEAT SHOCK PROTEIN PEPTIDES

CROSS-REFERENCE TO RELATED APPLICATION

This nonprovisional application claims benefit of priority under 35 U.S.C. §119(e) of provisional applications U.S. Ser. No. 61/281,178, filed Nov. 13, 2009, the entirety of which are hereby incorporated by reference.

FEDERAL FUNDING LEGEND

This invention was produced in part using funds obtained through a federal grant under No. AI31431. Consequently, the federal government has certain rights in this invention.

BACKGROUND OF THE INVENTION

1. Field of the Invention

The present invention relates generally to the fields of microbiology, bacteriology and molecular biology. More specifically, the present invention relates to compositions and methods for *Ehrlichia* diagnostics and therapeutics.

2. Description of the Related Art

The term ehrlichiosis has been broadly applied to a variety of diseases of humans and animals caused by pathogens classified in the genus *Ehrlichia*. *Ehrlichia chaffeensis* causes human monocytic ehrlichiosis (HME). Ehrlichiosis is transmitted by the bite of infected ticks, including the lone star tick. Ehrlichiosis cannot be spread from person to person.

Human monocytic ehrlichiosis, caused by *Ehrlichia chaffeensis*, was first reported in 1987. The clinical symptoms of human monocytic ehrlichiosis include fever, headache, malaise, myalgia, rash, lymphadenopathy, and nausea (Rikihisa, 1999). Human monocytic ehrlichiosis can be fatal to the immune compromised and elderly. White-tailed deer are presumed to be the reservoir hosts of *E. chaffeensis* (Dawson et al., 1994; Lockhart et al., 1997). Illness due to ehrlichiosis can be so mild that no medical care is sought or the illness can be severe and sometimes fatal. Symptoms are generally non-specific and other diagnoses may be considered. Because the laboratory tests that detect ehrlichiosis are often not positive in the first week of illness, physicians base early patient treatment decisions on the signs and symptoms, as well as the patient's history. The physician also looks at specific blood tests to help determine the likelihood of ehrlichiosis. Clues such as a low platelet count (thrombocytopenia), low serum sodium levels (hyponatremia), abnormal white blood cell counts (elevated or decreased), or elevated liver enzyme levels are often helpful predictors.

Serologic assays are the most frequently used methods for confirming cases of ehrlichiosis. The indirect immunofluorescence assay (IFA) is generally considered the reference standard in ehrlichiosis serology. Other assays include ELISA, latex agglutination, and dot immunoassays. Serologic tests can be used to detect either IgG or IgM antibodies. Blood samples taken early (acute) and late (convalescent) in the disease are the preferred specimens for evaluation. Most patients demonstrate increased IgM titers by the end of the first week of illness, but IgM assays may be falsely elevated due to other bacterial infections. IgG antibodies are considered more accurate for the ehrlichiosis, but detectable levels of IgG antibody generally do not appear until 7-10 days after the onset of illness. It is important to consider the amount of time it takes for antibodies to appear when ordering laboratory tests, especially because most patients visit their physician relatively early in the course of the illness, before diagnostic antibody levels may be present. The value of testing two sequential serum or plasma samples together to show a rising antibody level is important in confirming acute infection with ehrlichiosis. Because antibody titers may persist in some individuals for years after the original exposure, only demonstration of recent changes in titers between paired specimens can be considered reliable confirmation of an acute infection.

The most rapid and specific diagnostic assays for ehrlichiosis rely on molecular methods like PCR which can detect DNA present in a whole blood or tissue sample. PCR on whole blood specimens taken early during illness have been shown to be a very effective tool to diagnose ehrlichiosis. Immunostaining procedures can also be performed on formalin-fixed tissue samples. Ideally, whole blood or skin biopsy specimens used for diagnosis should be taken before or within the first 48 hours after doxycycline treatment is started; after antibiotic therapy has been started, it becomes more difficult to detect the organisms by these methods.

Canine ehrlichiosis is a disease of dogs and wild canids (e.g., wolves) and is found worldwide. Canine ehrlichiosis is also known by other names such as 'tracker dog disease,' 'tropical canine pancytopenia,' 'canine hemorrhagic fever,' and 'canine typhus.' Canine monocytic ehrlichiosis (CME) is an important tick-borne disease of dogs worldwide that is caused primarily by the obligatory intracellular organism *Ehrlichia canis* (Neer et al., 2002). *E. chaffeensis* can also infect dogs and several wild animals (Dawson et al., 1996) (Table 1). *E. canis* causes canine monocytic ehrlichiosis and was first recognized in Algeria in 1935 (Buhles et al., 1974). Wild and domestic dogs with chronic infection serve as reservoir hosts. During the acute phase of infection, the clinical signs include fever, anorexia, and lymphadenopathy, and, in the chronic phase of infection, the dogs may show emaciation, hemorrhage, and peripheral edema (Buhles et al., 1974).

Two blood tests that detect the dog's antibodies to *Ehrlichia* are available. One is called the indirect immunofluorescent antibody (IFA) test, and the other is ELISA test. A veterinarian cannot rely solely on these tests to make a diagnosis. The antibodies may not be detected in the early phase of the disease, since it takes some time for the body to make them. Also, if a dog is extremely ill, it may not be able to produce enough antibodies to be accurately detected. A positive test demonstrates that the dog has been exposed to *Ehrlichia*, but not that it necessarily is currently infected. In the acute stage of the disease, the antibody level will rise significantly. Often two tests will be done 2 weeks apart and the results compared. Dogs with an active infection will show a significant rise in the amount of antibody present. The antibodies can last for one or more years after the infection, but they do not make the dog immune to ehrlichiosis—the dog could get reinfected. Techniques using PCR tests for the presence of the organism itself, not antibodies to it. Unfortunately, it does not distinguish between live and dead organisms. For this reason, it is generally recommended to perform the PCR along with one of the antibody tests to make a diagnosis. There is no vaccine for ehrlichiosis currently.

The prior art is deficient in compositions and methods to diagnose and treat ehrlichiosis. The present invention fulfills this long-standing need and desire in the art.

SUMMARY OF THE INVENTION

The term ehrlichiosis has been broadly applied to a variety of diseases of humans and animals caused by pathogens classified in the genus *Ehrlichia*. The obligately intracellular bacterium *Ehrlichia chaffeensis* that resides in mononuclear phagocytes is the causative agent of human monocytotropic ehrlichiosis, whereas *Ehrlichia canis* causes ehrlichiosis in dogs. The present invention demonstrated by Eastern blotting that Heat shock protein (Hsp60/GroEL) is the major antigenic protein of *Ehrlichia*. An *Ehrlichia* specific Hsp60 peptide was designed in silico and used to raise antibody in mice. The antibody raised against Hsp60 peptide could detect proteins of 100 kD, 70 kD, 60 kD, 45 kD, 30 kD and 15 kD in different species of *Ehrlichia*. As the peptide can induce network cross reactivity, it can be used in several applications including as a vaccine for ehrlichiosis, and also for probes for the detection of *Ehrlichia* in humans and animals by ELISA or PCR technique.

The instant invention is directed to an isolated and purified heat shock protein 60 (Hsp60) peptide having the amino acid sequence of SEQ ID NO:2.

The instant invention is also directed to peptides that are at least 95% homologous to the amino acid sequence of SEQ ID NO:2. Preferably, the present invention also encompasses peptides that are at least 90% homologous to the amino acid sequence of SEQ ID NO:2, peptides that are at least 85% homologous to the amino acid sequence of SEQ ID NO:2 as well as peptides that are at least 80% homologous to the amino acid sequence of SEQ ID NO:2.

The instant invention is also directed to a vaccine against *Ehrlichia* comprising a peptide homologous to the amino acid sequence of SEQ ID NO:2.

The instant invention is also directed to an antibody directed against a peptide homologous to the amino acid sequence of SEQ ID NO:2.

The instant invention is also directed to a method of determining whether a subject is infected with *Ehrlichia*, comprising the steps of: contacting a sample from a subject with the antibody described herein; and detecting a resulting antibody reaction, wherein a positive reaction indicates the subject is infected with *Ehrlichia*.

The instant invention is also directed to a serodiagnostic kit for determining whether a subject is infected with *Ehrlichia*, said kit comprising: (a) the antibody described herein linked to a reporter molecule; (b) a buffer; and c) a reagent for detection of the reporter molecule.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings.

These drawings form a part of the specification. It is to be noted, however, that the appended drawings illustrate preferred embodiments of the invention and therefore are not to be considered limiting in their scope.

FIG. 1A: Western blot analyses of splenocytes of mice infected with *E. muris*, IOE and DH82 infected with *E. muris* probed with Hsp60 (GroEL) antibody. FIG. 1B: Western blot analyses of *E. canis* and *E. chaffeensis* infected DH82 cells.

DETAILED DESCRIPTION OF THE INVENTION

Figure 1B:
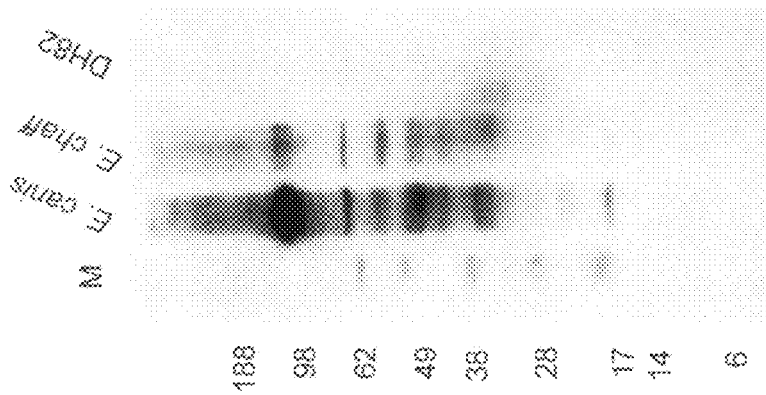
FIG. 1A-1B shows Western blot analyses using the Hsp60 antibody.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "replicon" is any genetic element (e.g., plasmid, chromosome, virus) that functions as an autonomous unit of DNA replication in vivo; i.e., capable of replication under its own control. A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix.

This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically. A "primer" is capable of acting as a point of initiation of synthesis when placed under conditions in which synthesis of a primer extension product, which is complementary to a nucleic acid strand, is induced (i.e., in the presence of nucleotides and an inducing agent such as a DNA polymerase and at a suitable temperature and pH). The primer may be either single-stranded or double-stranded and must be sufficiently long to prime the synthesis of the desired extension product in the presence of the inducing agent. The exact length of the primer will depend upon many factors, including temperature, source of primer and intended use. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two sequences are "substantially homologous" when at least about 75% (preferably at least about 80%, and most preferably at least about 90% or 95%) of the residues match over the defined length of the sequences. Sequences that are substantially homologous can be identified by comparing the sequences using standard software available in sequence data banks.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "host" is meant to include not only prokaryotes but also eukaryotes such as yeast, plant and animal cells. A recombinant DNA molecule or gene which encodes the peptide of SEQ ID NO. 2 of the present invention can be used to transform a host using any of the techniques commonly known to those of ordinary skill in the art.

Prokaryotic hosts may include *E. coli, S. typhimurium, Serratia marcescens* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes that are capable of providing phenotypic selection in transformed cells. The transformed hosts can be fermented and cultured according to means known in the art to achieve optimal cell growth.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA that is part of a hybrid gene encoding additional polypeptide sequence, e.g., a fusion protein.

The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods, which are well known to those skilled in the art, can be used to construct expression vectors containing appropriate transcriptional and translational control signals. See for example, the techniques described in Sambrook et al., 1989, Molecular Cloning: A Laboratory Manual (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein that has been separated from at least some of those components that naturally accompany it. Typically, the protein is substantially pure when it is at least 60%, by weight, free from the proteins and other naturally occurring organic molecules with which it is naturally associated in vivo. Preferably, the purity of the preparation is at least 75%, more preferably at least 90%, and most preferably at least 99%, by weight. A protein is substantially free of naturally associated components when it is separated from at least some of those contaminants that accompany it in its natural state. Thus, a protein that is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Other carriers may include a variety of lymphokines and adjuvants such as IL2, IL4, IL8 and others.

Means for conjugating a polypeptide to a carrier protein are well known in the art and include glutaraldehyde, m-maleimidobenzoyl-N-hydroxysuccinimide ester, carbo-diimide and bis-biazotized benzidine. It is also understood that the peptide may be conjugated to a protein by genetic engineering techniques that are well known in the art.

As is also well known in the art, immunogenicity to a particular immunogen can be enhanced by the use of nonspecific stimulators of the immune response known as adjuvants. Exemplary and preferred adjuvants include complete BCG, Detox, RIBI (Immunochem Research Inc.), ISCOMS and aluminum hydroxide adjuvant (Superphos, Biosector).

As used herein the term "complement" is used to define the strand of nucleic acid which will hybridize to the first nucleic acid sequence to form a double stranded molecule under stringent conditions. Stringent conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of formamide in the hybridization mixture.

As used herein, the term "engineered" or "recombinant" cell is intended to refer to a cell into which a recombinant gene, such as a gene encoding an antigen has been introduced. Therefore, engineered cells are distinguishable from naturally occurring cells that do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

Thus, in one embodiment, the present invention provides an isolated and purified heat shock protein 60 (Hsp60) peptide having the amino acid sequence of SEQ ID NO:2. In one aspect, the peptide may be dispersed in a pharmaceutically acceptable composition.

A person having ordinary skill in this art would readily be able to manipulate the peptide of SEQ ID NO. 2 in order to derive slightly different peptides with the same functions and uses as the peptide of SEQ ID NO. 2. Accordingly, the present invention also encompasses peptides that are at least 95% homologous to the amino acid sequence of SEQ ID NO:2. Preferably, the present invention also encompasses peptides that are at least 90% homologous to the amino acid sequence of SEQ ID NO:2, peptides that are at least 85% homologous to the amino acid sequence of SEQ ID NO:2 as well as peptides that are at least 80% homologous to the amino acid sequence of SEQ ID NO:2.

In one aspect of this embodiment of the present invention, the peptide may further comprise a label. In one aspect of this embodiment of the present invention, the peptide is chemically synthesized. In one aspect of this embodiment of the present invention, the peptide is produced in a cell. The peptide may further comprise a carrier. Further, the peptide may be conjugated to said carrier. For example, the protein and carrier may be conjugated by glutaraldehyde, m-maleimidobenzoyl-N-hydroxy-succinimide ester, carbo-diimide or bis-biazotized benzidine. Representative examples of useful carriers include keyhole limpet hemocyanin (KLH), human serum albumin, a lymphokine, or an adjuvant. Representative examples of useful adjuvants include IL2, IL4, IL8, BCG, Detox, RIBI, ISCOMS, or aluminum hydroxide.

In another embodiment, the present invention provides a vaccine against *Ehrlichia* comprising a peptide homologous to the amino acid sequence of SEQ ID NO:2. Representative species of *Ehrlichia* include *Ehrlichia chaffeensis, Ehrlichia muris, Ehrlichia ewingii, Ehrlichia ruminantium* and *Ehrlichia canis*.

In another embodiment, the present invention provides an antibody directed against a peptide homologous to the amino acid sequence of SEQ ID NO:2.

In another embodiment, the present invention provides a method of determining whether a subject is infected with *Ehrlichia*, comprising the steps of: contacting a sample from a subject with the antibody of the present invention; and detecting a resulting antibody reaction, wherein a positive reaction indicates the subject is infected with *Ehrlichia*. In one aspect of this embodiment of the present invention, the subject is a dog. In one aspect of this embodiment of the present invention, the sample is serum. Generally, the *Ehrlichia* is selected from the group consisting of *Ehrlichia chaffeensis, Ehrlichia muris* and *Ehrlichia canis*.

In another embodiment, the present invention provides a serodiagnostic kit for determining whether a subject is infected with *Ehrlichia*, said kit comprising: (a) the antibody described herein linked to a reporter molecule; (b) a buffer; and c) a reagent for detection of the reporter molecule. Representative reporter molecules include those selected from the group consisting of luciferase, horseradish peroxidase, P-galactosidase, and fluorescent labels.

The following examples are given for the purpose of illustrating various embodiments of the invention and are not meant to limit the present invention in any fashion.

*Ehrlichia muris* and *Ixodes ovatus ehrlichia* (IOE) are genetically related *Ehrlichia* species used in mouse models of ehrlichial infection. Though *E. muris* is mildly virulent, the *Ixodes ovatus ehrlichia* pathogen causes severe disease in mice. Using Eastern blotting, it was demonstrated that the heat shock protein, GroEL of *E. muris* has increased post-translational modifications than the highly virulent IOE (Thomas et al., 2009). The GroEL (heat shock proteins-Hsp's) are seen in all three domains of life—Bacteria, Archaea, and Eukarya (Woo et al., 2001) and are recognized as important molecules during pathological infections (Ueki et al., 2002). GroEL proteins are also immunomodulatory and are known to stimulate monocytes and macrophages (Galdiero et al., 1997, Ueki et al., 2002). An *E. muris*-specific Hsp60 antibody was generated and used it to observe the pathogen in cell culture.

Example 1

Design of Hsp60 Peptide

When examining a protein sequence for potential antigenic epitopes, it is important to choose sequences that are hydrophilic, surface-oriented, and flexible. Most naturally occurring proteins in aqueous solutions have their hydrophilic residues on the protein surface and hydrophobic residues buried in the interior. This optimization is based on the fact that antibodies tend to bind to epitopes on the protein surface. Additionally, it has been shown that epitopes have a high degree of mobility. When designing a peptide for antibody production, the first task is to decide upon the desired location of the antibody binding site on the protein of interest. Hydropathy plots of the amino acid sequence can be performed to determine the hydrophilicity of various regions of the protein (Kyte and Doolittle, 1982). Because hydrophilic regions are more likely to be exposed on the protein, an anti-peptide antibody to a hydrophilic sequence will be more likely to recognize the protein. Also, hydrophilic peptides dissolve more easily in aqueous solutions and so are easier to work with.

Three regions of the *E. muris* Hsp60 protein sequence had good hydrophilicity using the Lasergene software (DNAStar, Wis., USA). The peptides corresponded to amino acids 43-63, 179-199, 387-406 (Table 1).

Example 2

Generation of Hsp60 Antibody and Western Blotting

All the three peptides were conjugated to KLH (Biosynthesis, Texas) and 200 micrograms of each peptide was injected to 5 mice. Mice were injected with a initial dose of Hsp60 peptide combined with Freund's complete adjuvant and two doses of peptide combined with Freund's incomplete adjuvant. Injections were given 15 days apart and blood collected after 15 days of the last injection.

For western blotting, *E. muris*, *E. canis* and *E. chaffeensis* were cultivated in DH82 cells at 37° C. in DMEM supplemented with 5% heat inactivated bovine calf serum. Ehrlichiae were harvested when approximately 90 to 100% of the cells were infected. To produce infectious stocks for western blotting, C57BL/6 mice were inoculated i.p. with 1 ml of a $10^{-1}$ dilution ($5 \times 10^8$ *E. muris* or IOE) of the frozen stock. On day 7 after inoculation, the mice were sacrificed, the spleens were harvested, and splenic homogenate was prepared and suspended in DMEM medium. After centrifugation at 11,000 g the cells were suspended in PBS. The total protein concentrations of the resulting bacterial preparations were determined using a bicinchoninic acid protein assay kit (Pierce, Rockford, Ill.). DH82 cells or uninfected mouse spleen was used as the negative control.

Example 3

Immunomicroscopy for the Detection of Ehrlichia

For immunomicroscopy, DH82 infected with *E. muris* or *E. chaffeensis* or splenocytes from mouse infected with *E. muris* and IOE were used. After fixation both *E. muris*- and *E. chaffeensis*-infected DH82 cells were probed with the Hsp60 antibody (1:125) (45 min) and after several washes they were reacted with anti-mouse immunoglobulin G conjugated to Alexa 488.

Example 4

Synthesis of a Novel Peptide for the Production of Antibody to Detect *Ehrlichia*

Of the three peptides synthesized for the production of antibody only the peptide corresponding to the amino acid 43-63 of the Hsp60 protein elicited antibody production in mice. The sequence of the Hsp60 peptide is: YGAPEITKDGYKVIKSIKPED (SEQ ID NO. 2)

TABLE 1

*E. muris* GroEL (Hsp60) protein sequence
(SEQ ID NO. 1)

```
  1 manvvvtgeq ldksirevvr iledavgcta gpkgltvais ksygapeitk dgykviksik 61 pedplalaia niitqsasqc ndkvgdgttt csiltakvie evskakaaga divcikegvl 121 kakeavleal msmkrevlse eeiaqvatis angdknigsk iaqcvqevgk dgvitveesk 181 gfkeldvekt dgmqfdrgyl spyfvtnsek mlvefenpyi lltekklnii qpilpilenv 241 arsgrpllii aedvegeals tlvlnklrgg lhvaavkapg fgdrrkdmlg diailtgakh 301 visddlaikm edltlaelgt akniritkdt ttiigsvdns stnvqsrinq ikmqieasts 361 dydkeklrer laklsggvav lkvggsseve vkerkdrved alhatraave
```

The underlined peptides were synthesized for studies herein.

Analysis of the peptide showed homology to other Ehrlichial species.

TABLE 2

BLAST analysis of the Hsp60 peptide.

| Sequences producing significant alignments: | (Bits) | Value |
|---|---|---|
| gb\|DQ672553.1\| *Candidatus Ehrlichia* ovata groESL operon, part . . . | 46.2 | 0.003 |
| dbj\|AB032711.1\| *Ehrlichia* sp. Anan groEL gene for heat shock . . . | 46.2 | 0.003 |
| gb\|AF210459.1\|AF210459 *Ehrlichia muris* chaperonin GroEL (groE . . . | 46.2 | 0.003 |
| dbj\|AB032712.1\| *Ehrlichia* sp. HF565 groEL gene for heat shock . . . | 46.2 | 0.003 |
| dbj\|AB454077.1\| *Ehrlichia* sp. NS101 GroEL gene for heat shock . . . | 46.2 | 0.003 |
| gb\|CP000107.1\| *Ehrlichia canis* str. Jake, complete genome | 46.2 | 0.003 |
| gb\|U96731.1\|ECU96731 *Ehrlichia canis* GroES (groES) and GroEL . . . | 46.2 | 0.003 |
| gb\|FJ966349.1\| Uncultured *Ehrlichia* sp. clone Kh-Hj27 heat sh . . . | 45.8 | 0.004 |
| gb\|CP000236.1\| *Ehrlichia chaffeensis* str. Arkansas, complete . . . | 45.4 | 0.004 |
| gb\|L10917.1\|EHRHSP *Ehrlichia chaffeensis* heat shock protein (. . . | 45.4 | 0.004 |
| gb\|AF195273.1\|AF195273 *Ehrlichia ewingii* groESL operon, parti . . . | 45.4 | 0.004 |
| gb\|FJ966353.1\| Uncultured *Ehrlichia* sp. clone Khabarovsk 1931 . . . | 45.4 | 0.004 |
| gb\|FJ966351.1\| Uncultured *Ehrlichia* sp. clone Khabarovsk 362 . . . | 45.4 | 0.004 |
| gb\|DQ647014.1\| *Ehrlichia ruminantium* strain Kumm1 10 kDa chap . . . | 44.7 | 0.009 |
| gb\|DQ647004.1\| *Ehrlichia ruminantium* strain Kiswani 10 kDa ch . . . | 44.7 | 0.009 |
| emb\|CR925678.1\| *Ehrlichia ruminantium* str. Welgevonden, compl . . . | 44.7 | 0.009 |
| emb\|CR925677.1\| *Ehrlichia ruminantium* str. Gardel, complete g . . . | 44.7 | 0.009 |
| emb\|CR767821.1\| *Ehrlichia ruminantium* strain Welgevonden, com . . . | 44.7 | 0.009 |
| gb\|U13638.1\|CRU13638 *Cowdria ruminantium* Welgevonden heat sho . . . | 44.7 | 0.009 |
| gb\|DQ647013.1\| *Ehrlichia ruminantium* strain Kumm2 10 kDa chap . . . | 44.7 | 0.009 |
| gb\|DQ647012.1\| *Ehrlichia ruminantium* strain Blaauwkrans 10 kD . . . | 44.7 | 0.009 |
| gb\|DQ647009.1\| *Ehrlichia ruminantium* strain Mali 10 kDa chape . . . | 44.7 | 0.009 |
| gb\|DQ647008.1\| *Ehrlichia ruminantium* strain Senegal 10 kDa ch . . . | 44.7 | 0.009 |
| gb\|DQ647007.1\| *Ehrlichia ruminantium* strain Sankat 10 kDa cha . . . | 44.7 | 0.009 |
| gb\|DQ647005.1\| *Ehrlichia ruminantium* strain Umbanein 10 kDa c . . . | 44.7 | 0.009 |
| gb\|DQ647003.1\| *Ehrlichia ruminantium* strain Ball3 10 kDa chap . . . | 44.7 | 0.009 |
| gb\|DQ647010.1\| *Ehrlichia ruminantium* strain Mara87/7 10 kDa c . . . | 44.3 | 0.009 |
| dbj\|AB074462.1\| *Candidatus Ehrlichia shimanensis* GroEL gene f . . . | 44.3 | 0.010 |
| gb\|EF633745.1\| *Candidatus Neoehrlichia lotoris* strain RAC413 . . . | 43.9 | 0.015 |
| gb\|DQ647011.1\| *Ehrlichia ruminantium* strain Vosloo 10 kDa cha . . . | 43.5 | 0.018 |
| gb\|DQ647006.1\| *Ehrlichia ruminantium* strain Pokoase 10 kDa ch . . . | 43.1 | 0.024 |

Figure 1A:
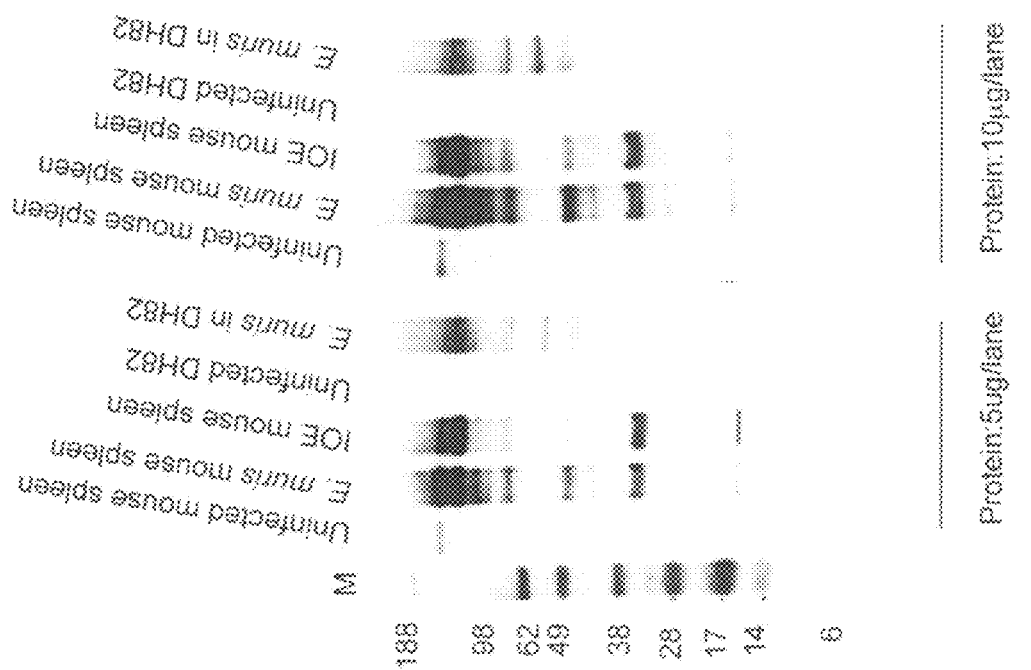
Figure 2:
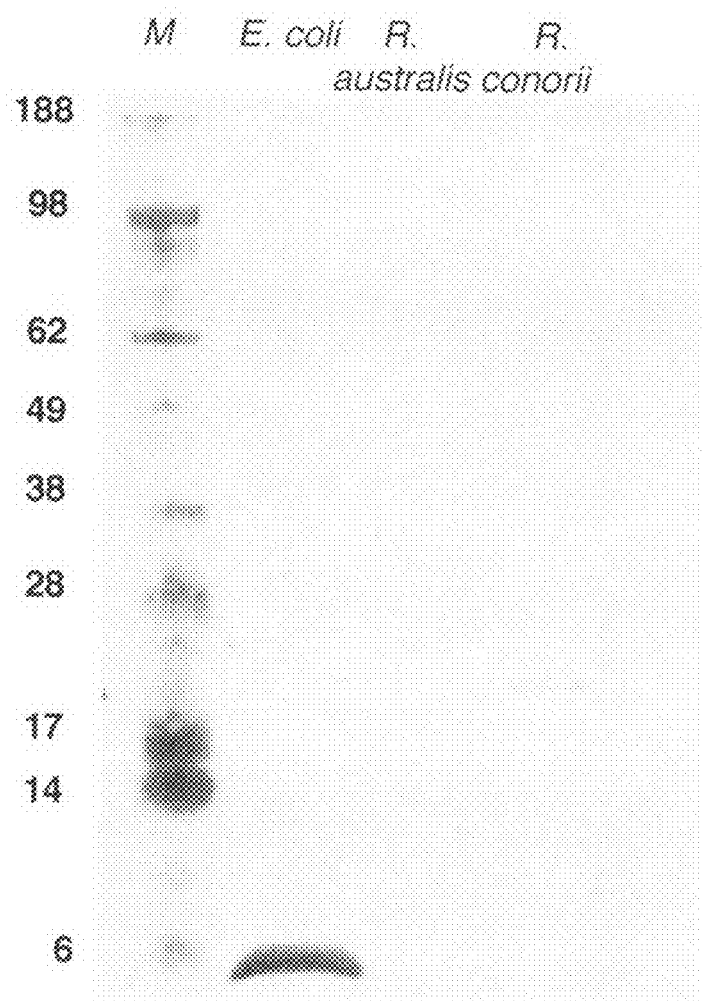
FIG. 2: Western blot analyses of *R. conorii*, *R. australis* and *E. coli* probed with Hsp60 (GroEL) antibody.

Western blotting of *Ehrlichia* using the antibody generated against *E. muris* Hsp60 peptide could detect 100, 70, 60, 45, 30 and 15 kDa proteins in *E. muris*, and IOE (FIG. 1A). The Hsp60 peptide antibody detected 100, 70, 60, and 45 kDa of *E. chaffeensis*, and *E. canis* cell lysate (FIG. 1B). The peptide did not detect the proteins in *E. coli* or in *Rickettsia australis* and *R. conorii* (FIG. 2). The results demonstrate that the antibody is specific for the detection of different *Ehrlichia* species.

Example 4

Detection of *Ehrlichia* by Immuno-Fluorescence Microscopy

The intracellular pathogens *E. chaffeensis* and *E. muris* are maintained in vitro in the DH82 monocyte cell line. *E. muris*- and *E. chaffeensis*-infected in DH82 cells were probed with the Hsp60 antibody. The Hsp60 antibody could detect *E. muris* and *E. chaffeensis* in DH82 cells. Finally, the antibody was probed for *E. muris* or IOE infected mouse splenocytes after 5 days of culture.

Figure 3:
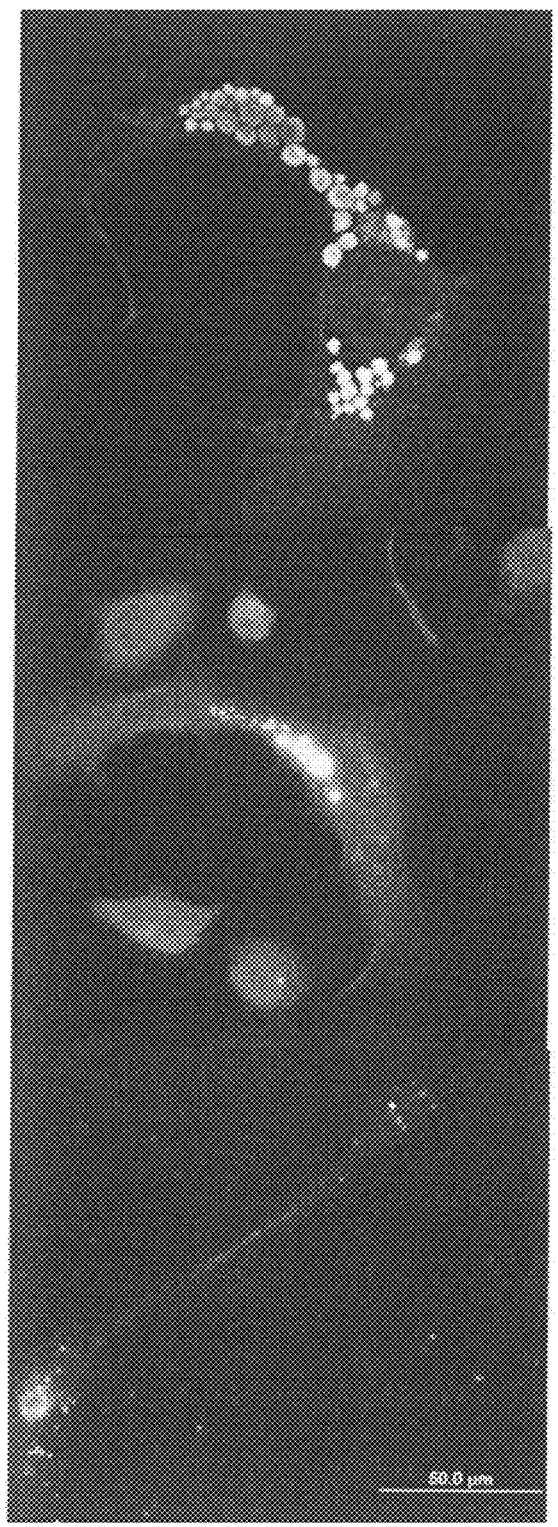
FIG. 3: Detection of *Ehrlichia* by immunofluorescence microscopy. The antibody raised against Hsp60 could detect *E. muris*, *E. chaffensis* and IOE in the host cell.

The antibody detected pathogens in mouse macrophages (FIG. 3). The results demonstrate that the Hsp60 antibody could be used to detect *Ehrlichia* pathogens in vivo.

Example 5

*Ehrlichia* Hsp60 as a Vaccine to Protect Against Ehrlichiosis

Figure 4:
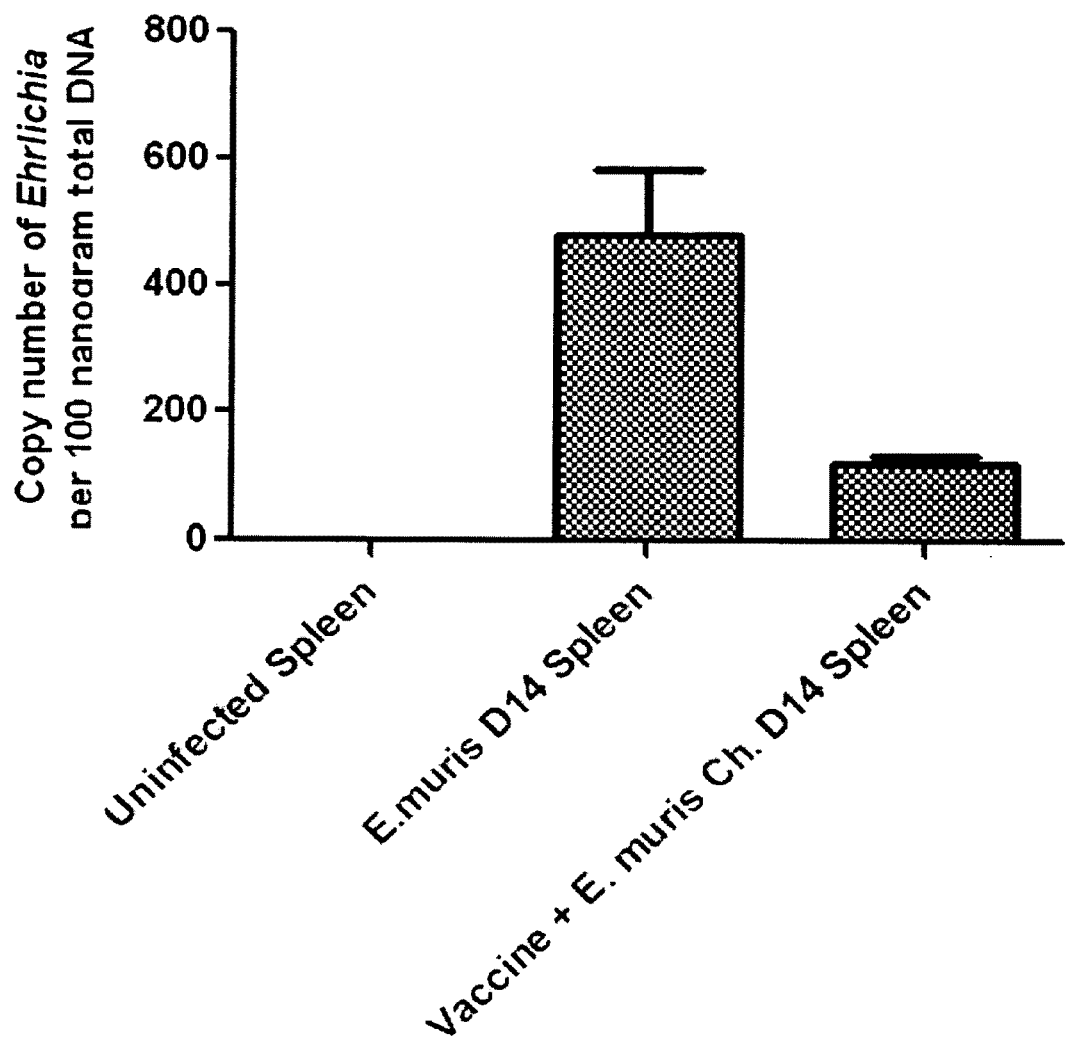
FIG. 4 shows vaccination with *Ehrlichia* Hsp60 decreased the bacterial load in *E. muris* challenged mice.

Mice were immunized with two doses of *Ehrlichia* Hsp60 (50 micrograms per dose) two weeks apart and later challenged with *E. muris*. The bacterial burden was detected by quantitative real time PCR in spleen and liver 14 days after bacterial challenge. FIG. 4 shows that the bacterial load was significantly reduced in *Ehrlichia* Hsp 60 vaccinated mice than the unvaccinated controls.

Figure 5A:
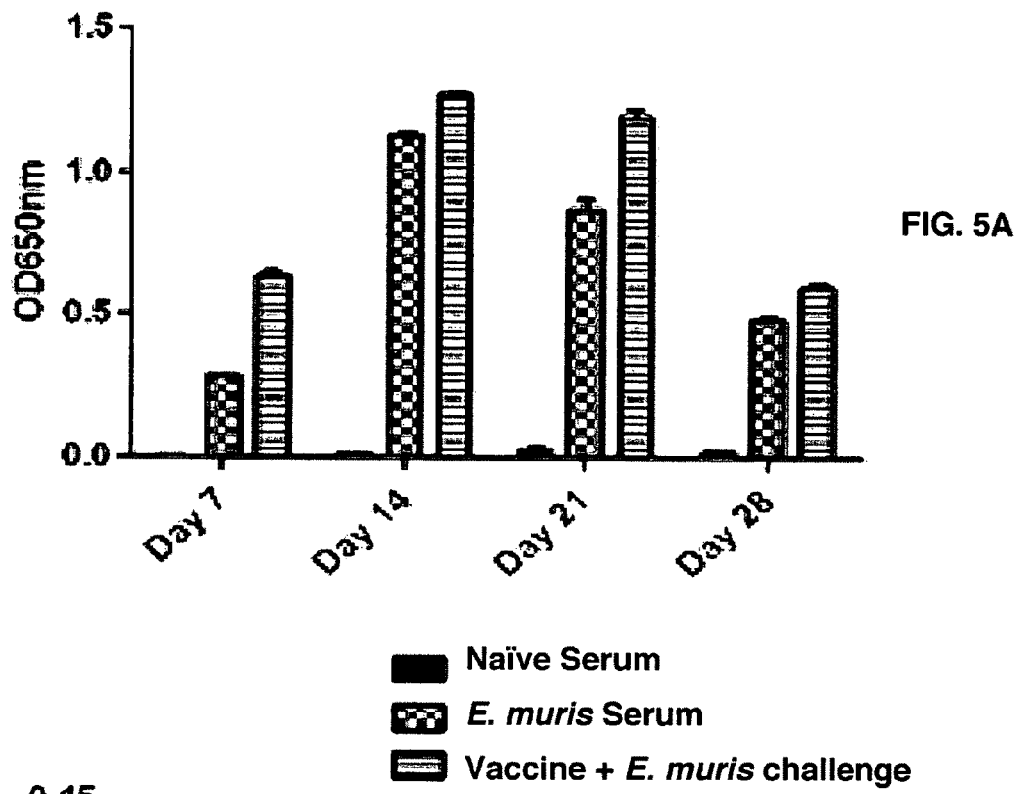
FIGS. 5A-5B show an analysis of IgM and IgG2b in *E. muris* (FIG. 5A) and *Ehrlichia* Hsp60 vaccine+*E. muris* challenged mice (FIG. 5B).
Figure 5B:
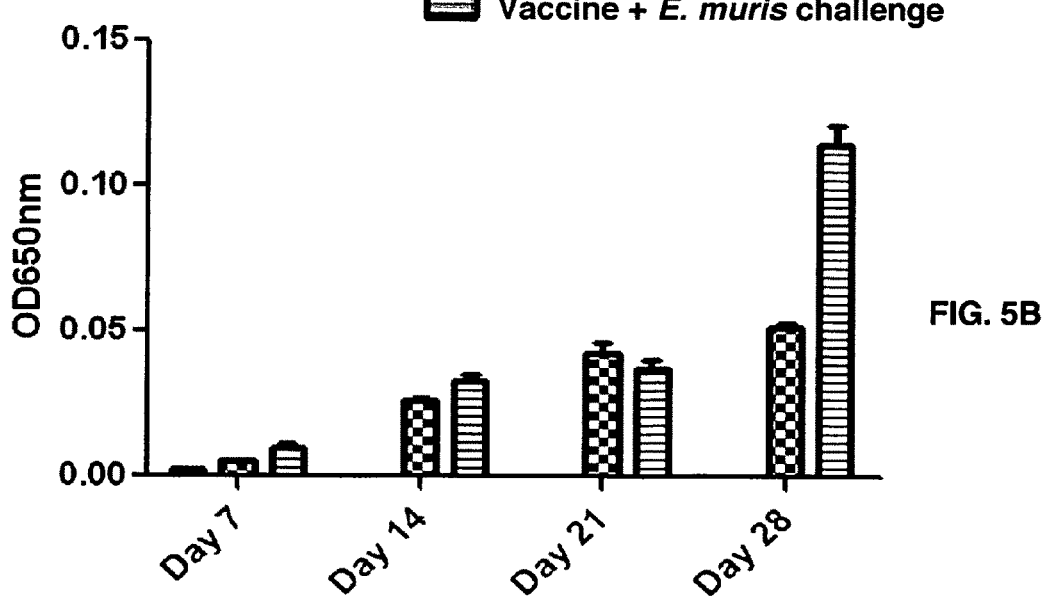

A major activator of classical complement protein is antibody of both IgG and IgM isotypes. IgM is necessary for recognition and activation of complement. C57BL/6 mice infected with *E. muris* or immunized with *Ehrlichia* HSP60 peptide vaccine and challenged with *E. muris* demonstrated that the concentration of IgM antibodies against *Ehrlichia* is enhanced compared to IgG subtypes (FIG. 5A,5B). The concentration of IgM in the serum of both *E. muris* and vaccinated mice (Vaccine+*E. muris* challenged) was the highest at day 14 after infection.

Figures 6A, 6B, 6C:
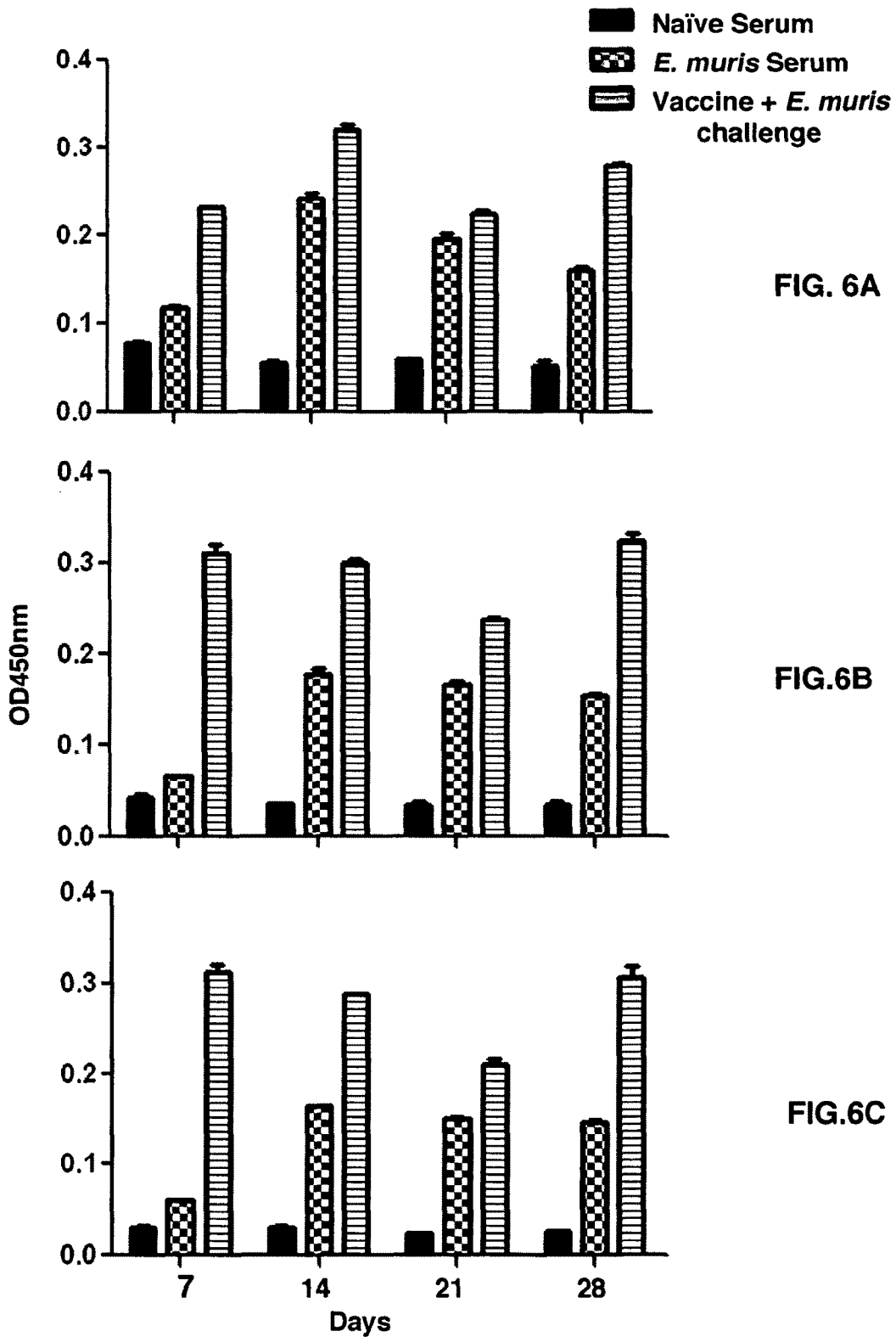
FIGS. 6A-6C show ELISA detection of C1q (FIG. 6A), C3a (FIG. 6A) and C5a (FIG. 6C) in the serum of *E. muris* and vaccine+*E. muris* challenged mice.

*Ehrlichia* Hsp60 increased complement protein synthesis. Analysis of the complement proteins C1q, C3a and C5a demonstrated that they are upregulated by day 14 (FIG. 6A-6C). The enhanced reduction of bacteria by day 14 may be due to the potency of the complement protein working in tandem with the antibodies as seen in the enhancement of IgM and complement proteins on day 14.

Figure 7:
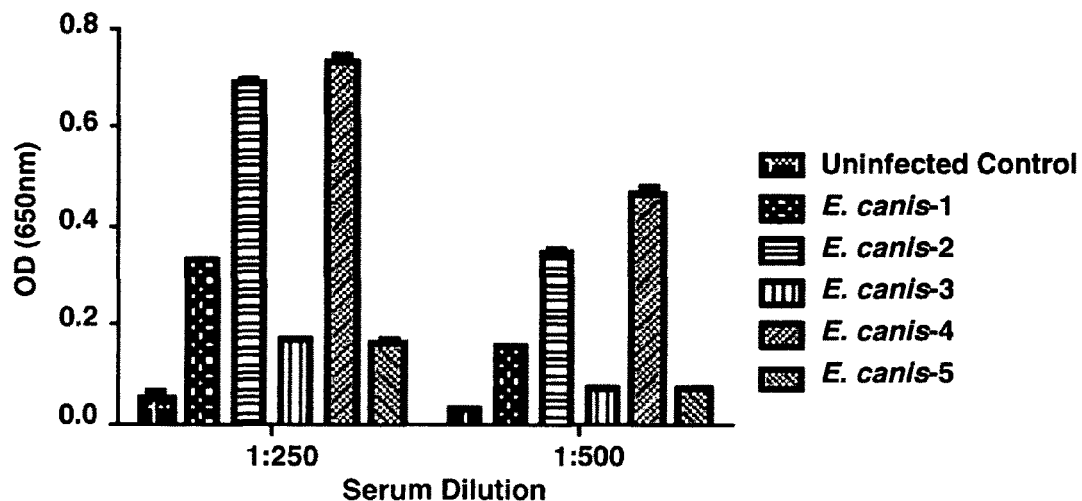
FIG. 7: Detection of *Ehrlichia canis* antibody in dogs by ELISA. The Hsp60 peptide was coated on to a Maxisorp ELISA plate (Nunc, Denmark) and later incubated with sera of dogs infected with *E. canis* (1:250 or 1:500). Finally they were probed with the secondary antibody-AP conjugate (1:1500). The graph represents the mean of three replicates.
Figure 8:
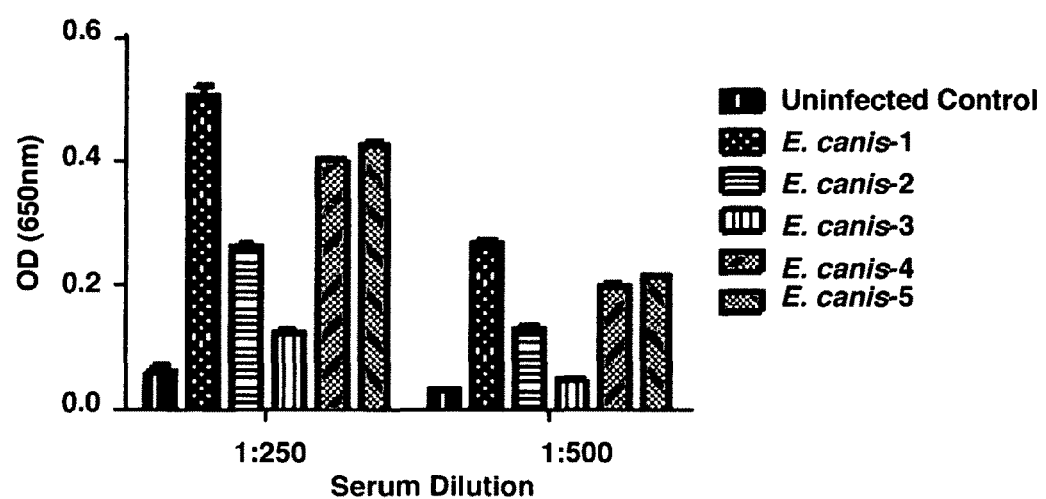
FIG. 8: Detection of *Ehrlichia chaffeensis* antibody in dogs by ELISA. The Hsp60 peptide was coated on to a Maxisorp ELISA plate (Nunc, Denmark) and later incubated with sera of dogs infected with *E. chaffeensis* (1:250 or 1:500). Finally they were probed with the secondary antibody-AP conjugate (1:1500). The graph represents the mean of three replicates.
Figure 9:
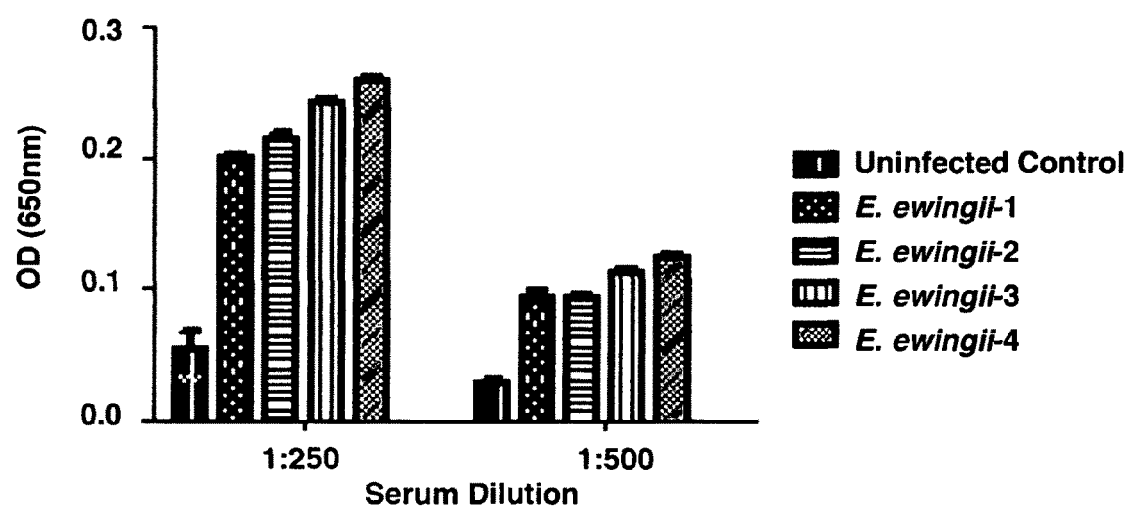
FIG. 9: Detection of *Ehrlichia ewingii* antibody in dogs by ELISA. The Hsp60 peptide was coated on to a Maxisorp ELISA plate (Nunc, Denmark) and later incubated with sera of dogs infected with *E. ewingii* (1:250 or 1:500). Finally they were probed with the secondary antibody-AP conjugate (1:1500). The graph represents the mean of three replicates.

FIGS. 7-9 present data illustrating the detection of *Ehrlichia canis* antibody in dogs by ELISA, the detection of *Ehrlichia chaffeensis* antibody in dogs by ELISA and the detection of *Ehrlichia ewingii* antibody in dogs by ELISA.

Heat shock proteins (HSPs) are molecular chaperones essential for maintaining cellular functions by preventing misfolding and aggregation of nascent polypeptides and by facilitating protein folding. Recently, heat shock proteins such as Hsp60, Hsp70, Hsp90, and gp96 [endoplasm reticulum (ER) form of Hsp90] have also been reported to play important roles in antigen presentation, activation of lymphocytes and macrophages, and activation and maturation of dendritic cells (APCs). Thus, it has been suggested that heat shock proteins provide the link between innate and adaptive immune system and that their presence in the circulation serves as danger signals to the host. No other molecules have been reported to possess such protean immune effects (Tsan and Gao, 2009).

Most Hsp60 proteins share a common oligomeric structure consisting of two stacked rings of seven subunits each. The co-operating factor GroES (Hsp10) binds asymmetrically to GroEL, and stimulates ATP hydrolysis and substrate release (Hartl, 1996). The Hsp proteins are highly conserved in nature from bacteria to humans (Harboe and Quayle, 1991). The immunological activities of Hsp60 in infectious diseases (Harboe & Quayle, 1991), in autoimmune reactions (Van Eden et al., 1989; Young, 1992), in cancer (Jäättelä & Wissing, 1992) as well as their use as potential anti-tumour vaccines (Ahsan & Sasaki, 1991, 1993) are active fields of investigation.

The present invention demonstrates that the Ehrlichial Hsp60 (GroEL) peptide is highly conserved and the antibody raised against the peptide only detects Ehrlichial proteins. Cellebaut et al. (1994) had demonstrated that domain III is common to Hsp60, Hsp70 and Hsp90. Quintana et al., (2004a,b) has demonstrated network cross-reactivity between Hsp60, Hsp70 and Hsp90. They demonstrated that DNA vaccination with HSP70 or HSP90 inhibited arthritogenic response, controlled adjuvant arthritis and also induced cross-reactive immune response to HSP60. The results herein also show that the antibody raised against Hsp60 peptide could detect proteins of 100 kD, 70 kD, 60 kD, 45 kD, 30 kD and 15 kD. As the peptide can induce network cross reactivity it could be used as a vaccine in ehrlichiosis. The advantage of the Hsp60 peptide vaccine is that it can induce network cross reactivity and elicit more immune response. When a vaccinated host is challenged by *Ehrlichia* (pathogen) the host may recognize all the heat shock proteins that are related or cross reacts with Hsp60 and induce a immune response leading to control of the pathogen. Noll and Autenrieth (1996) has demonstrated that Hsp60 can act as a subunit vaccine against *Yersinia enterocolitica*. The antibody raised against the peptide can also be used in ELISA to probe for *Ehrlichia*. The DNA sequence of the peptide could also be used to detect *Ehrlichia* by polymerase chain reaction technique (PCR).

Peptides bound or linked to heat-shock proteins of microbial or mammalian origin have been shown to elicit potent antigen-specific immunity. Some members of the heat shock protein family, such as Hsp60, Hsp70, Hsp90 and gp96, are able also to stimulate cells of the innate immune system directly and thus, act as 'danger'-signaling molecules. This effect is independent of heat shock protein-associated peptides and, in many respects, resembles the effect of lipopolysaccharide (LPS) (Wallin et al., 2002).

In addition to maintaining cell homeostasis under physiological and stress conditions, some heat shock proteins are potent inducers of immunity and have been harnessed as vaccine adjuvants targeted to cancers and infections. Certain heat shock proteins are potent inducers of innate and antigen-specific immunity. They activate dendritic cells partly through toll-like receptors, activate natural killer cells, increase presentation of antigens to effector cells and augment T-cell and humoral immune responses against their associated antigens. Their roles in priming multiple host defense pathways are being exploited in vaccine development for cancer and infectious diseases (Segal et al., 2006). Woo et al. (2001) has demonstrated that GroEL (Hsp60) is a highly antigenic protein in *Burkholderia pseudomallei*, which causes melioidosis. Patients with melioidosis develop a strong antibody response against GroEL, suggesting that the recombinant protein and its monoclonal antibody may be useful for serodiagnosis in patients with melioidosis (Woo et al., 2001).

The following references were cited herein:
Ahsan et al., FEBS Lett. 1991; 288:77-80.
Breitschwerdt, E B. Obligate intracellular pathogens. In Ettinger, S J; Feldman, E C (eds). Textbook of Veterinary Internal Medicine. W.B. Saunders Co. Philadelphia, Pa.; 2005; 631-632.
Buhles W C Jr, et al., J Infect Dis. 1974; 130:357-367.
Callebaut I et al., C R Acad Sci III. 1994; 317:721-729.
Couto, D. Rickettsial Diseases. In Birchard et al., (eds.) Saunders Manual of Small Animal Practice. W.B. Saunders Co. Philadelphia, Pa.; 1994; 124-125.
Dawson et al., Am J Vet Res. 1996; 57:1175-1179.
Dawson et al., J Clin Microbiol. 1994; 32: 2725-2728.
Galdiero et al., Infect Immun. 1997; 65: 699-707.
Harboe M, et al., Clin Exp Immunol. 1991; 86: 2-5
Harrus, et al. Canine monocytic ehrlichiosis: An update. Compendium of Continuing Education for the Veterinary Practitioner. 1997; 19: 431-444.
Hayer-Hartl et al., EMBO J. 1996; 15: 6111-6121.
Jäättelä et al., Ann Med. 1992; 24:249-258.
Kyte et al., J Mol. Biol. 1982; 157: 105-132.
Neer T M, et al., J Vet Intern Med. 2002; 16: 309-315.
Netzer W J, et al., Trends Biochem Sci. 1998; 23: 68-73.
Noll et al., Infect Immunity 1996; 64: 2955-2961.
Olson, J G. Ehrlichiosis. In: Zoonoses updates from the Journal of the American Veterinary Medical Association. American Veterinary Medical Association. Schaumburg, Ill.; 1995:74-75.
Quintana et al., 12th International Congress of Immunology and 4th Annual Conference of FOCIS, 2004a. pp 207-213.
Quintana et al., Arthritis Rheum. 2004b; 50: 3712-3720.
Rikihisa, Y et al., Microbes Infect. 1999; 1: 367-376.
Segal B H, et al., Drug Discov Today. 2006; 11: 534-540
Thomas et al., Parasite Immunol 2009; 31: 296-303.
Tsan et al., J Leuk Biol. 2009; 85: 905-910.
Ueki et al., Clin Exp Immunol. 2002; 127: 72-77.
Wallin R P, et al., Trends Immunol. 2002; 23: 130-135.
Woo et al., Clin Diagn Lab Immunol. 2001; 8: 832-836.
Woo P C, et al., Clin Diagn Lab Immunol. 2001; 8: 832-836.
Young D B. Heat-shock proteins: immunity and autoimmunity. Curr Opin Immunol. 1992; 4: 396-400.

Any patents or publications mentioned in this specification are indicative of the levels of those skilled in the art to which the invention pertains. These patents and publications are herein incorporated by reference to the same extent as if each individual publication was individually incorporated by reference.

One skilled in the art will readily appreciate that the present invention is adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated heat shock protein 60 peptide having at most 21 amino acids that is at least 80% identical to the amino acid sequence of SEQ ID NO:2.

2. The peptide of claim 1, wherein the amino acid sequence of the peptide is at least 90% identical to the amino acid sequence of SEQ ID NO:2.

3. The peptide of claim 1, wherein the amino acid sequence of the peptide is at least 95% identical to the amino acid sequence of SEQ ID NO:2.

4. The peptide of claim 1, wherein said peptide has the amino acid sequence of SEQ ID NO:2.

5. The peptide of claim 1, further comprising a label.

6. The peptide of claim 1, wherein said peptide further comprises a carrier.

7. The peptide of claim 6, wherein said peptide is conjugated to said carrier.

8. The peptide of claim 7, wherein said peptide and carrier are conjugated by glutaraldehyde, m-maleimidobenzoyl-N-hydroxy-succinimide ester, carbo-diimide or bis-biazotized benzidine.

9. The peptide of claim 6, wherein said carrier is keyhole limpet hemocyanin, human serum albumin, a lymphokine, or an adjuvant.

10. The peptide of claim 9, wherein the adjuvant is IL2, IL4, IL8, BCG, Detox, 5 RIBI, ISCOMS, or aluminum hydroxide.

11. A method of inducing an immune response against *Ehrlichia* comprising administering to a subject the peptide of claim 1.

12. The method of claim 11, wherein said *Ehrlichia* is selected from the group consisting of *Ehrlichia chaffeensis*, *Ehrlichia muris*, *Ehrlichia ewingii*, *Ehrlichia

SEQUENCE LISTING

<160> NUMBER OF SEQ ID NOS: 2

<210> SEQ ID NO 1
<211> LENGTH: 410
<212> TYPE: PRT
<213> ORGANISM: Ehrlichia muris
<220> FEATURE:
<223> OTHER INFORMATION: Hsp60 protein sequence

<400> SEQUENCE: 1

```
Met Ala Asn Val Val Val Thr Gly Glu Gln Leu Asp Lys Ser Ile
1               5                   10                  15

Arg Glu Val Val Arg Ile Leu Glu Asp Ala Val Gly Cys Thr Ala
                20                  25                  30

Gly Pro Lys Gly Leu Thr Val Ala Ile Ser Lys Ser Tyr Gly Ala
                35                  40                  45

Pro Glu Ile Thr Lys Asp Gly Tyr Lys Val Ile Lys Ser Ile Lys
                50                  55                  60

Pro Glu Asp Pro Leu Ala Leu Ala Ile Ala Asn Ile Ile Thr Gln
                65                  70                  75

Ser Ala Ser Gln Cys Asn Asp Lys Val Gly Asp Gly Thr Thr Thr
                80                  85                  90

Cys Ser Ile Leu Thr Ala Lys Val Ile Glu Glu Val Ser Lys Ala
                95                  100                 105

Lys Ala Ala Gly Ala Asp Ile Val Cys Ile Lys Glu Gly Val Leu
                110                 115                 120

Lys Ala Lys Glu Ala Val Leu Glu Ala Leu Met Ser Met Lys Arg
                125                 130                 135

Glu Val Leu Ser Glu Glu Glu Ile Ala Gln Val Ala Thr Ile Ser
                140                 145                 150

Ala Asn Gly Asp Lys Asn Ile Gly Ser Lys Ile Ala Gln Cys Val
                155                 160                 165

Gln Glu Val Gly Lys Asp Gly Val Ile Thr Val Glu Glu Ser Lys
                170                 175                 180

Gly Phe Lys Glu Leu Asp Val Glu Lys Thr Asp Gly Met Gln Phe
                185                 190                 195

Asp Arg Gly Tyr Leu Ser Pro Tyr Phe Val Thr Asn Ser Glu Lys
                200                 205                 210

Met Leu Val Glu Phe Glu Asn Pro Tyr Ile Leu Leu Thr Glu Lys
                215                 220                 225

Lys Leu Asn Ile Ile Gln Pro Ile Leu Pro Ile Leu Glu Asn Val
                230                 235                 240

Ala Arg Ser Gly Arg Pro Leu Leu Ile Ile Ala Glu Asp Val Glu
                245                 250                 255

Gly Glu Ala Leu Ser Thr Leu Val Leu Asn Lys Leu Arg Gly Gly
                260                 265                 270

Leu His Val Ala Ala Val Lys Ala Pro Gly Phe Gly Asp Arg Arg
                275                 280                 285

Lys Asp Met Leu Gly Asp Ile Ala Ile Leu Thr Gly Ala Lys His
                290                 295                 300

Val Ile Ser Asp Asp Leu Ala Ile Lys Met Glu Asp Leu Thr Leu
                305                 310                 315

Ala Glu Leu Gly Thr Ala Lys Asn Ile Arg Ile Thr Lys Asp Thr
                320                 325                 330
```

```
Thr Thr Ile Ile Gly Ser Val Asp Asn Ser Ser Thr Asn Val Gln
            335                 340                 345

Ser Arg Ile Asn Gln Ile Lys Met Gln Ile Glu Ala Ser Thr Ser
            350                 355                 360

Asp Tyr Asp Lys Glu Lys Leu Arg Glu Arg Leu Ala Lys Leu Ser
            365                 370                 375

Gly Gly Val Ala Val Leu Lys Val Gly Gly Ser Ser Glu Val Glu
            380                 385                 390

Val Lys Glu Arg Lys Asp Arg Val Glu Asp Ala Leu His Ala Thr
            395                 400                 405

Arg Ala Ala Val Glu
            410

<210> SEQ ID NO 2
<211> LENGTH: 21
<212> TYPE: PRT
<213> ORGANISM: artificial sequence
<220> FEATURE:
<222> LOCATION: 43..63
<223> OTHER INFORMATION: synthetic Hsp60 peptide

<400> SEQUENCE: 2

Tyr Gly Ala Pro Glu Ile Thr Lys Asp Gly Tyr Lys Val Ile Lys
1               5                   10                  15

Ser Ile Lys Pro Glu Asp
                20
```